United States Patent [19]

Karami

[11] 4,029,098
[45] June 14, 1977

[54] TAPE FASTENER FOR DISPOSABLE DIAPER
[75] Inventor: Hamzeh Karami, Crystal Lake, Ill.
[73] Assignee: Colgate-Palmolive Company, New York, N.Y.
[22] Filed: Nov. 10, 1975
[21] Appl. No.: 630,398
[52] U.S. Cl. .............................. 128/284; 128/287
[51] Int. Cl.² ......................................... A61F 13/16
[58] Field of Search ........................... 128/284, 287

[56] References Cited
UNITED STATES PATENTS

| | | | |
|---|---|---|---|
| 3,620,217 | 11/1971 | Gellert | 128/284 |
| 3,776,234 | 12/1973 | Hoey | 128/287 |
| 3,810,472 | 5/1974 | Aldinger et al. | 128/287 |
| 3,848,594 | 11/1974 | Buell | 128/284 |
| 3,875,621 | 4/1975 | Karami | 24/67 |

Primary Examiner—Aldrich F. Medbery
Attorney, Agent, or Firm—Powell L. Sprunger

[57] ABSTRACT

A disposable diaper comprising, an absorbent pad assembly having an absorbent pad, opposed surfaces, and at least one side edge. The diaper has a pressure-sensitive tape strip having an outer securement section for securing the diaper about an infant. The fastener has a sheet having an inner portion including a thermoplastic material secured to one of the surfaces of the pad assembly, with the sheet extending from the inner portion toward the side edge of the pad assembly.

21 Claims, 12 Drawing Figures

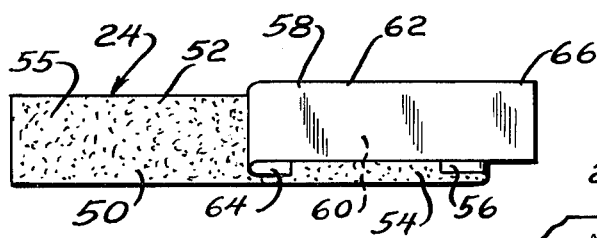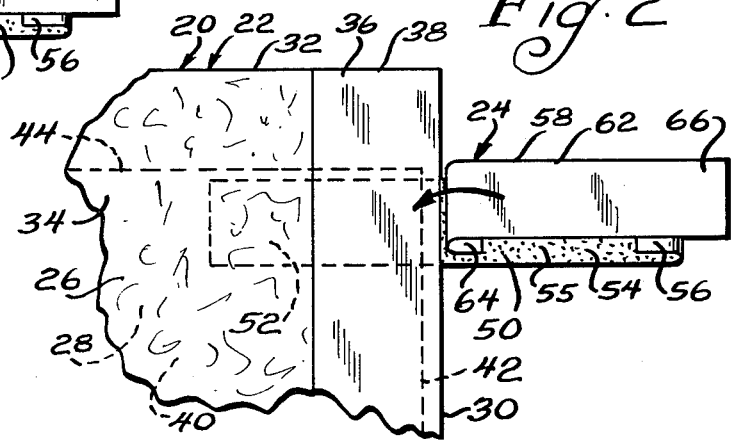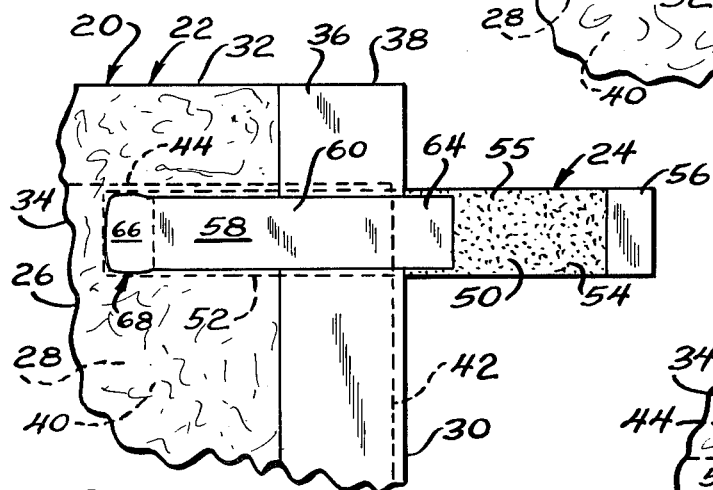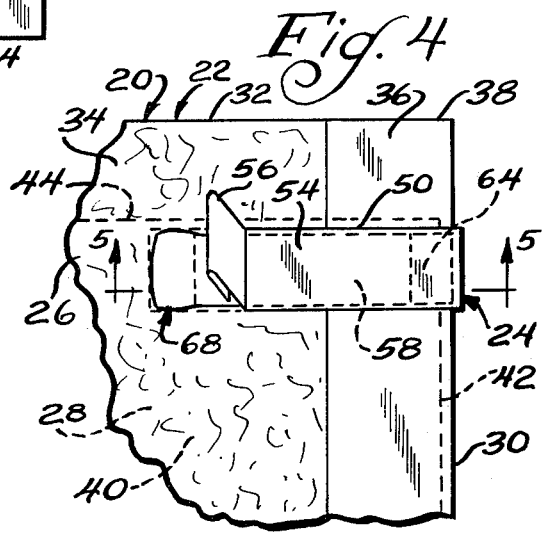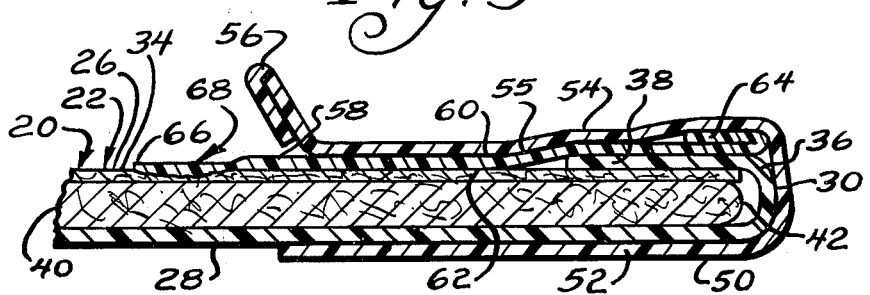

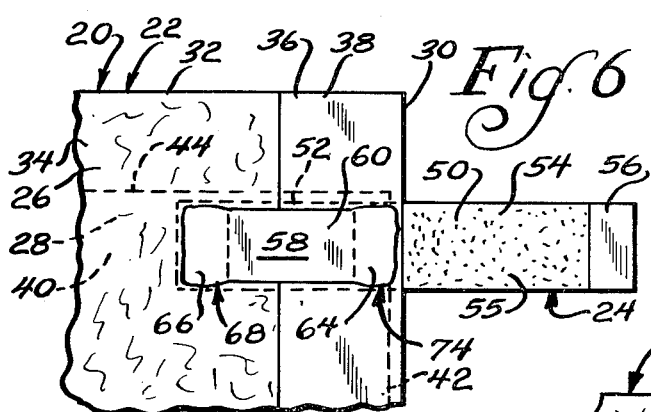

TAPE FASTENER FOR DISPOSABLE DIAPER

BACKGROUND OF THE INVENTION

The present invention relates to absorbent articles, and more particularly to disposable diapers.

A various assortment of disposable diapers have been proposed for use on infants. A number of such diapers have been provided with tape fasteners for securing the diaper about the infant during placement. The tape fasteners have generally taken the form of a tape strip having a securement portion which is covered by a release sheet, with the release sheet being removed from the securement portion of the tape strip during placement of the diaper to expose adhesive on the securement portion. While it has been found parents prefer that the release sheet be secured to the diaper itself to eliminate the necessity for discarding the release sheet, it is also desirable that the tape fastener be made of economic construction and easy to manufacture to reduce the cost of the diaper to the consumer.

SUMMARY OF THE INVENTION

A principal feature of the present invention is the provision of a tape fastener for a disposable diaper of simplified construction and reduced cost.

The diaper has an absorbent pad assembly having an absorbent pad, a back surface, a front surface, and at least one side edge. The tape fastener comprises, a pressure-sensitive tape strip having a first end section secured to the back surface of the pad assembly, and a second securement end section extending past the side edge of the pad assembly. The tape fastener has a sheet, such as a release sheet, having a first surface which may provide a relatively low affinity for adhesive on the tape strip. The sheet has an inner end including a thermoplastic material fused to the front surface of the pad assembly, with the sheet extending toward the side edge of the pad assembly.

In one embodiment, the sheet extends past the side edge of the pad assembly, with the outer end of the sheet being secured to adhesive on the second end section of the tape strip. In another embodiment, the sheet may include a thermoplastic material fused to the pad assembly adjacent the side edge to retain the outer end of the sheet to the pad assembly.

A feature of the present invention is that the sheet is permanently retained against the front surface of the pad assembly, and need not be discarded after placement of the diaper.

Another feature of the present invention is that the sheet is retained against the front surface of the pad assembly without the use of adhesive additional to that already included on the tape strip.

Thus, a feature of the invention is that the elimination of adhesive required to attach the sheet reduces the cost of the diaper.

Still another feature of the invention is that the adhesive free sheet may be fused or secured to the diaper in a simplified manner by high-speed manufacturing equipment.

Yet another feature of the invention is that the sheet may comprise a strip of thermoplastic material.

A further feature of the invention is that the sheet may comprise an outer strip of a first material and a thermoplastic material fused between the outer strip and the pad assembly.

A feature of the invention is that the fused thermoplastic material may comprise lateral side margins of a backing sheet for the pad assembly.

Another feature of the invention is that the fused material prevents severance of the sheet from the front surface of the pad assembly when wetted under use.

Further features will become more fully apparent in the following description of the embodiments of this invention and from the appended claims.

DESCRIPTIONS OF THE DRAWINGS

In the drawings:

FIG. 1 is a perspective view of a tape fastener according to the present invention prior to placement on a diaper;

FIG. 2 is a fragmentary plan view of a disposable diaper showing the tape fastener of FIG. 1 as partially applied to the diaper;

FIG. 3 is a fragmentary plan view of the diaper showing the tape fastener of FIG. 1 as secured to the diaper;

FIG. 4 is a fragmentary plan view of the diaper of FIG. 3 showing a securement portion of a tape strip releasably attached to a release sheet in the tape fastener;

FIG. 5 is a fragmentary sectional view taken substantially as indicated along the line 5—5 of FIG. 4;

FIG. 6 is a fragmentary plan view of a diaper showing another embodiment of the tape fastener of the present invention;

FIG. 7 is a fragmentary plan view of a diaper showing another embodiment of the tape fastener of the present invention;

FIG. 8 is a fragmentary sectional view of one embodiment of a release sheet for the tape fastener;

FIG. 9 is a fragmentary sectional view of an embodiment of a sheet for the tape fastener;

FIG. 10 is a fragmentary sectional view of an embodiment of a sheet for the tape fastener;

FIG. 11 is a fragmentary plan view of a diaper showing another embodiment of the tape fastener of the present invention; and FIG. 12 is a fragmentary sectional view taken substantially as indicated along the line 12—12 of FIG. 11.

DESCRIPTION OF THE PREFERRED EMBODIMENTS

Referring now to FIGS. 4 and 5, there is shown a disposable diaper generally designated 20 having an absorbent pad assembly 22 and a tape fastener 24 secured to the pad assembly 22. The pad assembly 22 has a front surface 26, a back surface 28, a side edge 30, and an end edge 32 connecting the side edge 30. The pad assembly 22 has a fluid pervious cover sheet 34 defining a substantial portion of the front surface 26 of the pad assembly, a fluid impervious backing sheet 36 defining the back surface 28 of the pad assembly and having lateral side margins 38 folded over and secured to the front surface 26 of the pad assembly, and an absorbent pad 40 intermediate the cover and backing sheets 34 and 36. The backing sheet is preferably made from a thermoplastic material, such as polyethylene. The absorbent pad 40 has a side edge 42 preferably located adjacent the side edge 30 of the pad assembly 22, and an end edge 44 connecting the side edge 42 and spaced from the end edge 32 of the pad assembly 22. It is understood that the opposed side of the diaper (not shown) would normally have a structure substantially similar to that described above, and would include a tape fastener as described below.

As shown in FIG. 1, the tape fastener 24 has an elongated pressure-sensitive tape strip 50 having a first fixed end section 52, a second securement end section 54, and adhesive 55 on one surface of the strip. The tape strip 50 may have a folded over end 56 adjacent the outer end of the second end section 54 defining tab means for a purpose which will be described below. The tape fastener 24 also has a release sheet 58 of a thermoplastic material, such as a strip of polyethylene, having a first surface 60 providing a release surface for the adhesive 55 on the tape strip 5, and a second opposed adhesive-free surface 62 which faces the front surface 26 of the pad assembly 22. The second surface 62 of an outer end 64 of the release sheet 58 is secured to the adhesive 55 on the second end section 54 of the tape strip 50, while the other inner end 66 of the release sheet may be secured to the front surface 26 of the pad assembly by sealing, as described below. Either the first surface 60 or the second surface 62 of the release sheet 58 may be treated, as desired, to obtain relative affinities for the adhesive 55.

As shown in FIG. 2, the first end section 52 of the tape strip 50 is secured to the back surface 28 of the pad assembly 22. As illustrated in FIGS. 2 and 3, the inner end 66 of the release sheet 58 is folded over the front surface 26 of the pad assembly 22, with the second surface 62 of the release sheet 58 facing the front surface 26 of the pad assembly. As shown, the inner end 66 of the release sheet 58 is sealed to the front surface 26 of the pad assembly in a zone 68 adjacent the inner end 66 in order to secure the inner end 66 of the release sheet to the pad assembly. The inner end 66 may be readily sealed to the pad assembly in any suitable manner, such as by application of heat with a heated die during the manufacturing procedure. In an embodiment, the cover sheet 34 may be made of a thermoplastic material, such as polyethylene, and the release sheet 58 may be made of any suitable material, such as paper, with the cover sheet being fused to the release sheet. Thus, the outer end 64 of the release sheet 58 is retained by the adhesive on the second end section 54 of the tape strip, while the inner end 66 is anchored against the front surface 26 of the pad assembly 22 by the seal zone 68. Accordingly, the release sheet 58 is retained against the front surface 26 of the pad assembly with no adhesive additional to that on the tape strip 50, thus reducing the cost of the diaper. Additionally, manufacture of the diaper is simplified, since the adhesive-free release sheet may be readily folded over and secured to the diaper by high-speed manufacturing sealing equipment without impediment by an adhesive bearing surface on the sheet and without application of adhesive.

As shown in FIGS. 3-5, the second end section 54 of the tape strip 50, including the outer end 64 of the release sheet 58, is folded over the front of the diaper and the second end section 54 of the tape strip 50 is releasably attached to the first surface 60 of the release sheet 58. Since the first surface 60 of the release sheet 58 has a relatively low affinity for the adhesive on the second end section 54 of the tape strip, the second end section of the tape strip may be readily removed from the release sheet 58 during placement of the diaper. Removal of the second end section 54 from the release sheet 58 is facilitated by the tab 56 at the outer end of the second end section, which is free of attachment to the release sheet 58 and the pad assembly 22. After the second end section 54 of the tape strip 50 is removed from the first surface 60 of the release sheet 58, in the position as shown in FIG. 3, the second end section 54 is properly located for securing the diaper 20 about the infant. Thus, securement of the diaper is accomplished without removal of the release sheet from the pad assembly, eliminating the necessity for separately discarding release sheets after placement of the diaper. Additionally, the seal zone 68 prevents severence of the release sheet 58 from the front surface of the pad assembly when it is wetted during use.

Another embodiment of the present invention is illustrated in FIG. 6, in which like reference numerals designate like parts. In this embodiment, the tape fastener 24 may have a second seal zone 74, which may also be formed by heat sealing, located adjacent the side edge 30 of the pad assembly, with the seal zone 74 extending transversely across the release sheet. In this embodiment, the outer end 64 of the release sheet 58 is located adjacent the side edge 30 of the pad assembly 22. Thus, the seal zone 74 retains the outer end 64 of the release sheet against the front surface 26 of the pad assembly 22, while the seal zone 68 retains the inner end 66 of the release sheet 58 against the pad assembly. Accordingly, the release sheet 58 is retained in place against the front surface of the pad assembly without the use of adhesive. Alternatively, the seal zone 74 may be omitted from the tape fastener, such that the outer end 64 of the release sheet 58 is free of attachment to the diaper. In this case, the seal zone 68 retains the release sheet 58 against the pad assembly with sufficient strength to prevent dislodgement of the release sheet from the diaper when the second end section 54 of the tape strip is peeled from the release sheet in a direction away from the zone 68.

Another embodiment of the present invention is illustrated in FIG. 7, in which like reference numerals designate like parts. In this embodiment, the release sheet has a seal zone 69 which extends the length of the release sheet between its inner and outer ends 66 and 64, respectively. As before, the seal zone 69 may be formed by heat sealing the release sheet to the pad assembly. It will also be apparent that the release sheet described in connection with FIGS. 1-5 may have a seal zone which extends from the inner end 66 of the release sheet 58 to a location adjacent the side edge 30 of the pad assembly, or may have spaced seal zones, as discussed in connection with FIG. 6.

Another embodiment of the invention is illustrated in FIG. 8, in which like reference numerals designate like parts. In this embodiment, the release sheet 58 has an outer strip 80, such paper, which may have its outer surface 60 treated, such as by silicone, to provide a release surface having a relatively low affinity for adhesive. The sheet 58 has a pair of spaced segments 82 and 84 of a thermoplastic material, such as polyethylene or a line of hot melt adhesive, located adjacent the inner and outer ends 66 and 64, respectively, of the strip 80. Either one or both ends 64 and 66 of the release sheet 58 may be heated to fuse the segments 82 and 84, such that the fused segments bond the strip 80 to the front surface of the pad assembly.

Another embodiment of the invention is illustrated in FIG. 9, in which like reference numerals designate like parts. In this embodiment, the release sheet 58 has an outer strip of material 80, such as paper, which is placed over the lateral side margin 38 of the thermoplastic backing sheet 36. The side margin 38 of the backing sheet may be heated through the strip 80 to fuse the strip 80 to the pad assembly. The strip 80 may be suitably treated to provide an outer release surface 60, as previously described.

Another embodiment of the invention is illustrated in FIG. 10, in which like reference numerals designate like parts. In this embodiment, the release sheet 58 has an outer strip 80 of a material, such as paper, which may have its outer surface 60 suitably treated to provide a release surface. The release sheet also has a strip 88 of thermoplastic material which extends between the inner and outer ends 66 and 64 of the release sheet, and which may be laminated to the strip 80. Any portion of the release sheet, including its entire length, may be heated to fuse the strip 80 to the front surface of the pad assembly.

Another embodiment of the present invention is illustrated in FIGS. 11 and 12, in which like reference numerals designate like parts. In this embodiment, a release sheet 72 is releasably attached to the adhesive on the second end section 54 of the tape strip 50. The release sheet 72 is removed from the second end section 54 during placement of the diaper to expose the underlying adhesive which is then used to secure the diaper about the infant. In this embodiment, the sheet 58' serves to obtain improved anchorage of the first end section 52 of the tape strip 50 to the diaper. The outer end 64 of the sheet 58' is secured to the tape strip 50 and the inner end 66 of the sheet 58' may be sealed to the pad assembly, as previously described, thus preventing the first end section 52 of the tape strip 50 strip 50 from being pulled away from the diaper. The release sheet described in connection with the diaper of FIGS. 1–5 also serves a similar function. Of course, the sheet 58' may have spaced zones or a continuous seal zone extending between the inner sheet end 66 to a location adjacent the side edge 30, as desired.

The foregoing detailed description is given for clearness of understanding only, and no unnecessary limitations should be understood therefrom, as modifications will be obvious to those skilled in the art.

I claim:
1. A disposable diaper, comprising:
   an absorbent pad assembly having an absorbent pad, opposed surfaces, and at least one side edge; and
   a tape fastener comprising, a pressure-sensitive tape strip having an outer securement section for securing the diaper about an infant, and a release sheet associated with the securement section and having an inner portion permanently joined to one of said surfaces of the pad assembly over the pad as a unitary piece by being fused with a heat sensitive plastic material, with said sheet extending from said inner portion toward said side edge of the pad assembly.
2. The diaper of claim 1 wherein said sheet comprises a strip of thermoplastic material having at least a portion fused to said one surface.
3. The diaper of claim 1 wherein said tape strip has an inner section secured to the other of said pad assembly surfaces, and in which said securement section extends from the inner section past said side edge of the pad assembly.
4. The diaper of claim 3 wherein an outer end of said sheet extends past the side edge of the pad assembly, with the outer end of said sheet being secured to adhesive on the securement section of tape strip adjacent said side edge.
5. The diaper of claim 4 wherein said strip securement section is releasably attached to an outer release surface of said sheet.
6. The diaper of claim 4 wherein said sheet has an inner end fused to said pad assembly.
7. The diaper of claim 1 wherein an outer end of the sheet is spaced from the strip securement section and located adjacent said side edge of the pad assembly, and in which the strip securement section is releasably attached to an outer release surface of said sheet.
8. The diaper of claim 7 wherein said outer end of said sheet is fused by thermoplastic material to said one surface of the pad assembly.
9. The diaper of claim 8 wherein said sheet is fused by thermoplastic material to said one surface of the pad assembly intermediate inner and outer ends of said sheet.
10. The diaper of claim 1 wherein said sheet includes an outer strip of a first material, and bonding means of a thermoplastic material intermediate said outer strip and one surface of said assembly.
11. The diaper of claim 10 wherein said bonding means comprises a segment of thermoplastic material adjacent an inner end of said sheet, said segment being fused to secure said inner end to the pad assembly.
12. The diaper of claim 8 wherein said sheet includes an outer strip of a first material, and bonding means of a thermoplastic material intermediate said outer strip and one surface of said pad assembly, and said bonding means comprises a segment of thermoplastic material adjacent said outer sheet end, said segment being fused to secure said outer end of the pad assembly.
13. The diaper of claim 9 wherein said sheet includes an outer strip of a first material, and bonding means of a thermoplastic material intermediate said outer strip and one surface of said pad assembly, and in which said bonding means comprises an inner strip of thermoplastic material extending between inner outer ends of said sheet, said inner strip being fused to secure said sheet to the pad assembly.
14. The diaper of claim 10 wherein said bonding means comprises a hot melt adhesive.
15. The diaper of claim 1 in which said pad assembly includes a thermoplastic backing sheet, and in which the fastener sheet is fused by lateral side margins of said backing sheet.
16. The diaper of claim 1 wherein said sheet has an outer release surface having a relatively low affinity for adhesive on the said strip securement section, said securement section being releasably attached to said sheet release surface.
17. The diaper of claim 1 in which said pad assembly includes a thermoplastic cover sheet, and in which the fastener sheet is fused by said cover sheet.
18. The diaper of claim 1 wherein said sheet has an inner end fused to said pad assembly.
19. A disposable diaper, comprising:
   an absorbent pad assembly having an absorbent pad and opposed surfaces;
   a pressure-sensitive tape strip having a securement section for securing the diaper about an infant; and
   a release sheet having an outer release surface for releasable attachment of said strip securement section to said release surface, said release sheet having at least a portion permanently joined to one of said surfaces of the pad assembly over the pad as a unitary piece by being fused with a heat sensitive plastic material.

20. The diaper of claim 19 wherein said release sheet comprises a strip of thermoplastic material, with at least a portion of said strip being fused to the pad assembly.

21. The diaper of claim 19 wherein said release sheet comprises, an outer strip of a first material defining said release surface, and a thermoplastic material intermediate said outer strip and said one surface being fused to secure the outer strip to the pad assembly.

* * * * *